United States Patent
van der Bruggen et al.

(10) Patent No.: US 6,353,089 B1
(45) Date of Patent: *Mar. 5, 2002

(54) METHOD FOR STIMULATING CTLS WITH PEPTIDES

(75) Inventors: Pierre van der Bruggen; Thierry Boon-Falleur, both of Brussels (BE); Catia Traversari; Katharina Fleischauer, both of Milan (IT)

(73) Assignee: Ludwig Institute for Cancer Research, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,797

(22) Filed: Jul. 7, 1999

Related U.S. Application Data

(62) Division of application No. 08/668,560, filed on Jun. 21, 1996, now Pat. No. 6,019,987, which is a division of application No. 08/217,187, filed on Mar. 24, 1994, now Pat. No. 5,554,506.

(51) Int. Cl.$^7$ .................................................. C07K 7/06
(52) U.S. Cl. ................ 530/328; 424/184.1; 424/185.1; 424/193.1; 424/277.1; 514/15
(58) Field of Search ............................ 530/328; 514/15; 424/185.1, 184.1, 193.1, 277.1

(56) References Cited

U.S. PATENT DOCUMENTS

| | | | | |
|---|---|---|---|---|
| 5,342,774 A | * | 8/1994 | Boon | 435/240.2 |
| 5,405,940 A | * | 4/1995 | Boon | 530/328 |
| 5,462,871 A | * | 10/1995 | Boon-Falleur | 435/240.2 |
| 5,554,506 A | * | 9/1996 | van der Bruggen | 435/7.24 |
| 5,585,461 A | * | 12/1996 | Townsend | 530/325 |
| 5,686,068 A | * | 11/1997 | Melief | 424/93.71 |

OTHER PUBLICATIONS

Bjorkman, Nature 329, 512, 1987.*

* cited by examiner

*Primary Examiner*—Christopher S. F. Low
*Assistant Examiner*—David Lukton
(74) *Attorney, Agent, or Firm*—Fulbright & Jaworski, LLP

(57) ABSTRACT

Tumor rejection antigens derived from tumor rejection precursor MAGE-3 have been identified. These "T-RAS" bind to the MHC-class I molecule HLA-A2, and the resulting complexes stimulate the production of cytolytic T cell clones which lyse the presenting cells. The peptides and complexes may be used diagnostically, therapeutically, and as immunogens for the production of antibodies, or as targets for the generation of cytolytic T cell clones.

4 Claims, No Drawings

METHOD FOR STIMULATING CTLS WITH PEPTIDES

This application is a divisional of Ser. No. 08/668,560, filed Jun. 21, 1996, now U.S. Pat. No. 6,019,987, which is it self a divisional of Ser. No. 08/217,187, filed Mar. 24, 1994, now U.S. Pat. No. 5,554,506.

FIELD OF THE INVENTION

This invention relates to immunogenetics and to peptide chemistry. More particularly, it relates to peptides, such as nonamers, decamers, and undecamers useful in various ways, including immunogens and as ligands for the HLA-A2 molecule. More particularly, it relates to a so-called "tumor rejection antigen", derived from the tumor rejection antigen precursor encoded by gene MAGE-3, and presented by MHC-class I molecule HLA-A2.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum variants fail to form progressive tumors because they initiate an immune rejection process. The evidence in favor of this hypothesis includes the ability of "tum–" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or nay not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 126: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum$^{31}$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum variants following mutagenesis, including variants referred to as P91A (DePlaen, supra), 35B (Szikora, supra), and P198 (Sibille, supra). In contrast to tumor rejection antigens—and this is a key distinction—the tum$^{31}$ antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce tum− variants. Since the tum− phenotype differs from that of the parent cell line, one expects a difference in the DNA of tum− cell lines as compared to their tum+ parental lines, and this difference can be exploited to locate the gene of interest in tum− cells. As a result, it was found that genes of tum− variants such as P91A, 35B and P198 differ from their normal alleles by point mutations in the coding regions of the gene. See Szikora and Sibille, supra, and Lurguin et al., Cell 58: 293–303 (1989). This has proved not to be the case with the TRAs of this invention. These papers also demonstrated that peptides derived from the tum− antigen are presented by the $L^d$ molecule for recognition by CTLs. P91A is presented by Ld, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Baringa, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that a particular nonapeptide is in fact presented on the surface of some tumor cells, and that the presentation of the nonapeptide requires that the presenting molecule be HLA-A1. Complexes of the MAGE-1 tumor rejection antigen (the "TRA" or nonapeptide") leads to lysis of the cell presenting it by cytolytic T cells ("ICTLs"). Attention is drawn, e.g., to, concurrently filed application Ser. No. 08/217,186 now U.S. Pat. No. 5,585,461 to Townsend, et al., and Ser. No. 08/217,186 now U.S. Pat. No. 5,554,724 to Melief, et al., both of which present work on other, MAGE-derived peptides. Research presented in, e.g., U.S. Pat. No. 5,405,940 and in U.S. Pat. No. 5,462,871, when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

These references, especially U.S. Pat. No. 5,462,871, showed a connection between HLA-A1 and RAGE-3; however, only about 26% of the Caucasian population and 17% of the negroid population presents HLA-A1 molecules on cell surfaces. Thus, it would be useful to have additional information on peptides presented by other types of MHC molecules, so that appropriate portions of the population may benefit from the research discussed supra.

It has now been found that antigen presentation of MAGE-3 derived peptides is not limited to HLA-A1 molecules. The invention set forth, in the disclosure which follows, identifies peptides which complex with MHC class I molecule HLA-A2. The ramifications of this discovery, which include therapeutic and diagnostic uses, are among the subjects of the invention, set forth in the disclosure which follows.

DETAILED DESCRIPTION OF PREFERRED EMBODIMENTS

EXAMPLE 1

The sequence of the MAGE-3 gene is known, as per Ser. No. 08/037,230, e.g., and PCT/US92/04354, e.g., both of which are referred to supra, and are incorporated by reference in their entirety. Similarly, it is known that HLA-A1-cells, transfected with a nucleic acid molecule coding for MAGE-3 are lysed by cytolytic T cells (see, e.g. Ser. No. 08/037,230, the disclosure of which is incorporated by reference in its entirety; also, see U.S. Pat. No. 5,462,871, the disclosure of which is incorporated by reference in its entirety).

These findings suggested a review of the amino acid sequence coded for by the MAGE-3 gene, together with the scoring system developed by Nijman et al., Eur. J. Immunol. 23: 1215 (1993), incorporated by reference in its entirety, to identify peptides derived from MAGE-3 which, putatively, bind to the HLA-A2 MHC molecule. This reference, in brief, describes a system where "anchor", "strong" and "weak" amino acids may be found along a peptide. Anchor positions are at the second and ninth amino acids. There are three possible positions where a strong amino acid can be placed, and four where a weak amino acid may be placed. The maximum score possible for a nonamer is $6^2 \times 4^3 \times 2^4$, or 36,864. Such peptides were identified, and are the peptides referred to hereafter.

EXAMPLE 2

The peptides identified via the protocol set forth supra were synthesized using a protein synthesizer, and were dissolved in 0.9% NaCl, 5% DMSO (or 5% DMF for the peptide SEQ ID NO: 3), at 0.5 mM. These peptide solutions were stored at −80° C. until ready for use.

To determine whether or not peptides bound to HLA-A2 molecules, cell line 174 CEM.T2 (hereafter "T2") was used. This cell line is described by Cerundolo et al., Nature 345: 449–452 (1990), and Spies et al., Nature 348: 744–747 (1990), the disclosures of which are incorporated by reference. This is a cell line deficient in the pathway which supplies peptides to the endoplasmic reticulum, the site of assembly of MHC class I heterodimers. It can assemble MHC class-I molecules, but these are unstable, and, on cell lysis, dissociate into free heavy and light chains during overnight incubation. The heterodimers can, however, be stabilized in vitro via addition of appropriate peptide ligands, as per Townsend et al., Nature 340: 443–448 (1989); Townsend et al., Cell 62: 285–195 (1990); Cerundolo et al., supra; Schumacher et al., Nature 350: 703–706 (1991); Elliot et al., Nature 351: 402–406 (1991); Elvin et al., Eur. J. Immunol. 21 : 2025–2031 (1991). The thus stabilized molecules can be immunoprecipitated with antibodies specific for the MHC class-I molecule.

In light of this background, the T2 cells were washed in serum free IMDM medium, and then $1.0 \times 10^6$ cells were suspended in 400 ul of the serum free IMDM medium, together with 100 ul synthetic peptide (final concentration: 0.1 mM, 1% DMSO). The mixture was incubated, overnight, at 37° C. Following incubation, the cells were washed and stained, successively, with HLA-A2 specific monoclonal antibody BB7.2, and FITC labelled, binding fragments of polyclonal goat anti-mouse IgG. Fluorescence ratio was calculated by the following formula:

$$\frac{\text{Mean fluorescence of the experimental sample}}{\text{Mean fluorescence of the background}}$$

This yielded the "mean fluorescence ratio" or MFR. In accordance with Nijman et al, supra, an MFR greater than 1.5 indicates binding to HLA-A2.

Five peptides were identified which were predicted to bind specifically to the HLA-A2 molecules. These five were tested in the assay described above, and three of them, i.e., SEQ ID NOS: 1, 3 and 4 were found to bind to HLA-A2 molecules. Each had an MFR value greater than the 1.5 value, i.e.

| Peptide | | MFR |
|---|---|---|
| M3-44.53 | TLVEVTLGEV (SEQ ID NO: 1) | 3.5 |
| M3-108.116 | ALSRKVAEL (SEQ ID NO: 2) | 2.17 (and, less than 1.5) |
| M3-195.203 | IMPKAGLLI (SEQ ID NO: 3) | 2.37 |
| M3-220.228 | KIWEELSVL (SEQ ID NO: 4) | 2.37 |
| M3-277.286 | ALVETSYVKV (SEQ ID NO: 5) | 1.8 (and, less than 1.5) |

The peptides M3108.116 and M3-277.286 had MFRs less than 1.5 in some of the experimental runs, and were-not considered further.

EXAMPLE 3

The results obtained in Example 2 suggested further experiments, and peptide M3-220.228 was used to generate a cytolytic T cell clone, referred to hereafter as CTL 4.2. The CTL clone was obtained using T2 cells, in accordance with Houbiers et al., Eur. J. Immunol. 23: 2072 (1993), previously incorporated by reference in its entirety.

Once the CTL clone was isolated, it was used in a chromium release assay in accordance with Boon, et al., J. Exp. Med. 152: 1184 (1980) the disclosure of which is incorporated by reference in its entirety. In addition to T2, cell line SK23, which is an HLA-A2 presenting line, was tested. The results are presented below:
Effector Cell (E): CTL 4.2 Target (T): HLA-A2 cell plus SEQ ID NO: 4

| | % $^{51}$CR Release | | | |
|---|---|---|---|---|
| E/T RATIO | T2 | T2 + peptide | SK23 | SK23 + Peptide |
| 30 | 0 | 91 | 0 | 35 |
| 7.5 | 0 | 88 | −1 | 33 |
| 1.9 | −1 | 84 | −1 | 14 |
| 0.5 | −1 | 57 | −1 | 2 |

These data show that target cells, pulsed with SEQ ID NO: 4, are specifically lysed by the cytolytic T cell clone 4.2. No lysis occurs in the absence of the peptide.

The foregoing describes the identification of peptides derived from the MAGE-3 tumor rejection antigen precursor which interact with MHC class I molecule HLA-A2. Of particular interest, and a part of the subject matter of the present invention, are the peptides represented by SEQ ID NO: 3 and SEQ ID NO: 4. These peptides are easily synthesized via Merrifield or other peptide synthesis methodologies, and thus isolated peptides of SEQ ID NO: 3 and SEQ ID NO: 4 are a feature of the invention described herein.

The peptides, as indicated, complex with HLA-A2 molecules, and these complexes have been immunoprecipitated, thus leading to another feature of the invention, which is isolated complexes of the HLA-A2 molecule and either one of these peptides.

Both the peptides and the complexes are useful in various ways. As was shown, the peptides bind to the HLA-A2 molecule, and thus they are useful in assays to determine whether or not HLA-A2 presenting cells are present in a sample. The peptide is contacted to the sample of interest in some determinable form, such as a labelled peptide (radiolabel, chromophoric label, and so forth), or bound to a solid phase, such as a column or an agarose or SEPHAROSE bead, and the binding of cells thereto determined, using standard analytical methods.

Both the peptides and the isolated complexes may be used in the generation of monoclonal antibodies or cytolytic T cell clones specific for the aforementioned complexes. Those skilled in the art are very familiar with the methodologies necessary to accomplish this, and the generation of a cytolytic T cell clone is exemplified supra. As cancer cells present complexes of MAGE-3 derived peptides of SEQ ID NO: 3 or SEQ ID NO: 4 and HLA-A2, these monoclonal antibodies and cytolytic T cells clones serve as reagents which are useful in diagnosing cancer. The chromium release assay discussed supra is exemplary of assays which use CTLs to determine targets of interest, and the art is quite familiar with immunoassays and how to carry these out.

Cytolytic T cell clones thus derived are useful in therapeutic milieux such as adoptive transfer. See Greenberg, J. Immunol. 136(5): 1917 (1986); Reddel et al., Science 257: 238 (1992); Lynch et al., Eur. J. Immunol. 21: 1403 (1991); Kast et al., Cell 59: 603 (1989), all of which are incorporated by reference herein. In this methodology, the peptides set forth supra are combined with antigen presenting cells ("APCs"), to form stable complexes. Many such methodologies are known, for example, those disclosed in Leuscher et al., Nature 351: 72–74 (1991); Romero et al., J. Exp. Med. 174: 603–612 (1991); Leuscher et al., J. Immunol. 148: 1003–1011 (1992); Romero et al., J. Immunol. 150: 3825–3831 (1993); Romero et al., J. Exp. Med. 177: 1247–1256 (1993), and Romero et al., U.S. patent application Ser. No. 133,407, filed Oct. 5, 1993 and incorporated by reference herein. Following this, the presenting cells are contacted to a source of cytolytic T cells to generate cytolytic T cell clones specific for the complex of interest. Preferably, this is done via the use of an autologous T cell clone, found in, for example, a blood sample, taken from the patient to be treated with the CTLs. Once the CTLs are generated, these are reperfused into the subject to be treated in an amount sufficient to ameliorate the cancerous condition, such as by lysing cancer cells, inhibiting their proliferation, etc.

Other aspects of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for stimulating proliferation of cytolytic T cells comprising contacting a cytolytic T cell containing sample with a cell presenting a complex of an HLA-A2 molecule and a peptide, the amino acid sequence of which consists of, SEQ ID NO: 4, for a time and under conditions effective to stimulate proliferation of cytolytic T cells specific for said complex.

2. The method of claim 1, comprising contacting said cytolytic T cell containing sample with said cell presenting a complex of an HLA-A2 molecule and a peptide in vitro.

3. The method of claim 1, comprising contacting said cytolytic T cell containing sample with said cell presenting a complex of an HLA-A2 molecule and a peptide in vivo.

4. The method of claim 1, wherein said T cell containing sample is a blood sample.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
       (A) LENGTH: 10 amino acid
       (B) TYPE: amino acids
       (D) TOPOLOGY: linear (ii) MOLECULE TYPE: protein (xi) SEQUENCE DESCRIPTION: SEQ ID NO: 1:

Thr Leu Val Glu Val Thr Leu Gly Glu Val
                  5                  10

(2) INFORMATION FOR SEQ ID NO: 2:

(i) SEQUENCE CHARACTERISTICS:
       (A) LENGTH: 9 amino acid
       (B) TYPE: amino acids
       (D) TOPOLOGY: linear (ii) MOLECULE TYPE: protein (xi) SEQUENCE DESCRIPTION: SEQ ID NO: 2:

Ala Leu Ser Arg Lys Val Ala Glu Leu
                  5

(2) INFORMATION FOR SEQ ID NO: 3:

(i) SEQUENCE CHARACTERISTICS:
       (A) LENGTH: 9 amino acid
       (B) TYPE: amino acids
       (D) TOPOLOGY: linear (ii) MOLECULE TYPE: protein (xi) SEQUENCE DESCRIPTION: SEQ ID NO: 3:

Ile Met Pro Lys Ala Gly Leu Leu Ile
                  5

(2) INFORMATION FOR SEQ ID NO: 4:

(i) SEQUENCE CHARACTERISTICS:
       (A) LENGTH: 9 amino acid
       (B) TYPE: amino acids
       (D) TOPOLOGY: linear (ii) MOLECULE TYPE: protein (xi) SEQUENCE DESCRIPTION: SEQ ID NO: 4:

Lys Ile Trp Glu Glu Leu Ser Val Leu
                  5

(2) INFORMATION FOR SEQ ID NO: 5:

(i) SEQUENCE CHARACTERISTICS:
       (A) LENGTH: 10 amino acid
       (B) TYPE: amino acids
       (D) TOPOLOGY: linear -continued

```
    (ii) MOLECULE TYPE: protein (xi) SEQUENCE DESCRIPTION:  SEQ ID NO: 5:

Ala Leu Val Glu Thr Ser Tyr Val Lys Val
                5                   10
```